(12) United States Patent
Ashida (10) Patent No.: US 8,657,754 B2
(45) Date of Patent: Feb. 25, 2014

(54) SPHYGMOMANOMETER

(75) Inventor: Tameo Ashida, Takatsuki (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 92 days.

(21) Appl. No.: 13/354,518

(22) Filed: Jan. 20, 2012

(65) Prior Publication Data

US 2012/0123281 A1 May 17, 2012

Related U.S. Application Data

(63) Continuation of application No. PCT/JP2010/062320, filed on Jul. 22, 2010.

(30) Foreign Application Priority Data

Jul. 23, 2009 (JP) ................... 2009-172408

(51) Int. Cl.
*A61B 5/022* (2006.01)

(52) U.S. Cl.
USPC ............................ 600/499; 600/490; 600/485

(58) Field of Classification Search
USPC ................................. 600/490–499
See application file for complete search history.

(56) References Cited

U.S. PATENT DOCUMENTS

| | | | |
|---|---|---|---|
| 2005/0187485 A1* | 8/2005 | Fumuro et al. | 600/499 |
| 2005/0192501 A1 | 9/2005 | Sano et al. | |
| 2008/0146948 A1* | 6/2008 | Fumuro et al. | 600/490 |
| 2008/0146950 A1* | 6/2008 | Fumuro et al. | 600/499 |
| 2011/0213256 A1* | 9/2011 | Taniguchi et al. | 600/493 |
| 2011/0245694 A1* | 10/2011 | Kukita et al. | 600/490 |

FOREIGN PATENT DOCUMENTS

| | | |
|---|---|---|
| CN | 1660010 A | 8/2005 |
| CN | 101229059 A | 7/2008 |
| JP | 57-180939 A | 11/1982 |
| JP | 3001683 U | 9/1994 |
| JP | 11-342117 A | 12/1999 |
| JP | 2005-237802 A | 9/2005 |
| JP | 2005-334125 A | 12/2005 |
| JP | 2008-148765 A | 7/2008 |
| JP | 3147041 U * | 12/2008 |
| JP | 2010075514 A * | 4/2010 |

OTHER PUBLICATIONS

International Search Report issued in PCT/JP2010/062320 mailed on Aug. 17, 2010 with English translation thereof, 4 pages.

(Continued)

*Primary Examiner* — Navin Natnithithadha
*Assistant Examiner* — Meredith Weare
(74) *Attorney, Agent, or Firm* — Osha Liang LLP (57) ABSTRACT

In a sphygmomanometer, an elbow detection mechanism that detects the placement of a measurement subject's elbow is provided in a portion of a cuff unit above a rotation axis. Because the elbow detection mechanism is provided in the portion of the cuff unit above the rotation axis on the biological member (upper arm) exit side, the distance L between the elbow detection mechanism and the biological member (upper arm) exit of the cuff unit can be kept constant even when the cuff unit rotates. This enables providing a sphygmomanometer that has a mechanism for changing the inclination angle of the cuff unit relative to a base and includes a mechanism for achieving a constant distance between the elbow detection mechanism and the entrance of the cuff unit regardless of the inclination angle of the cuff unit.

1 Claim, 10 Drawing Sheets

(56) References Cited

OTHER PUBLICATIONS

Patent Abstracts of Japan, Publication No. 2008-148765, Publication Date: Jul. 3, 2008, 1 page.
Patent Abstracts of Japan, Publication No. 11-342117, Publication Date: Dec. 14, 1999, 1 page.
Patent Abstracts of Japan, Publication No. 2005-334125, Publication Date: Dec. 8, 2005, 1 page.
Office Action issued in corresponding Chinese Application No. 201080032926.9 dated Jul. 15, 2013, and English translation thereof (11 pages).

* cited by examiner

SPHYGMOMANOMETER

TECHNICAL FIELD

The present invention relates to a sphygmomanometer for compressing and fixing a biological member, and in particular relates to a sphygmomanometer for blood pressure measurement that can compress and fix a biological member by automatically winding a cuff used in a sphygmomanometer or the like around the biological member (e.g., the upper arm).

BACKGROUND ART

The sphygmomanometer disclosed in JP 2008-148765A (Patent Document 1) includes a cuff unit serving as a measurement unit, and a base on which the elbow of an arm is placed after having passed through the cuff unit. The cuff unit is attached to the base such that its inclination angle relative to the horizontal plane can be changed.

An elbow detection mechanism for detecting the placement of an elbow is provided at a predetermined position on the base. The sphygmomanometer can measure the blood pressure of a measurement subject when the elbow detection mechanism has detected the placement of an elbow. However, even if the elbow of the measurement subject has passed through the cuff unit, the sphygmomanometer does not measure the blood pressure of the measurement subject if the elbow detection mechanism has not detected the placement of the elbow.

Consideration will now be given to the inclination angle of the cuff unit relative to the base, based on differences in the physiques of measurement subjects. If the measurement subject has a small physique, the position of their shoulders is lower than that of a measurement subject who has a large physique. For this reason, if their elbows are placed on the same horizontal plane, the inclination angle of the upper arm tends to be steep for a measurement subject who has a large physique and gentle for a measurement subject who has a small physique.

When an upper arm is inserted into the cuff unit of a sphygmomanometer having the above configuration, it is often the case that the inclination angle of the cuff unit relative to the base is larger if the measurement subject has a large physique, and that the inclination angle of the cuff unit relative to the base is smaller if the measurement subject has a small physique.

The elbow detection mechanism of the above-described sphygmomanometer is provided fixed at a predetermined position on the base, and a mechanism for changing the inclination angle of the cuff unit relative to the base is provided on the lower end side of the cuff unit. Consequently, the smaller the inclination angle of the cuff unit is, the greater the distance between the entrance of the cuff unit and the elbow detection mechanism is. For this reason, the distance to the elbow detection mechanism is longer for the measurement subject whose physique is small, regardless of the fact that the length of their upper arm is shorter than that of a measurement subject whose physique is large, and it is possible that this will be a cause for loss of an appropriate measurement posture.

Examples of other sphygmomanometers that include an elbow detection mechanism are disclosed in JP 3001683U (Patent Document 2) and JP H11-342117A (Patent Document 3). Also, another sphygmomanometer that includes an elbow holder is disclosed in JP 2005-334125A (Patent Document 4).

CITATION LIST

Patent Literature

Patent Document 1: JP 2008-148765A
Patent Document 2: JP 3001683U
Patent Document 3: JP H11-342117A
Patent Document 4: JP 2005-334125A

SUMMARY OF INVENTION

With a sphygmomanometer having a mechanism for changing the inclination angle of a cuff unit relative to a base, the distance between the entrance of the cuff unit and an elbow detection mechanism changes depending on the inclination angle of the cuff unit.

Accordingly, one or more embodiments of the present invention provide a sphygmomanometer that has a mechanism for changing the inclination angle of a cuff unit relative to a base, and includes a mechanism for achieving a constant distance between the entrance of the cuff unit and an elbow detection mechanism regardless of the inclination angle of the cuff unit.

A sphygmomanometer according to one or more embodiments of the present invention includes: a base; a cuff unit into which a biological member serving as a measurement site can be inserted; a rotation mechanism that is provided between the base and a position below a biological member exit side of the cuff unit and enables rotation of the cuff unit relative to the base about a rotation axis; and an elbow detection mechanism that is provided in a portion of the cuff unit above the rotation axis and detects placement of an elbow of a measurement subject.

According to this configuration of one or more embodiments of the present invention, it is possible to provide a sphygmomanometer including a mechanism that achieves a constant distance between the entrance of a cuff unit and an elbow detection mechanism regardless of the inclination angle of the cuff unit.

DETAILED DESCRIPTION OF INVENTION

The following describes a sphygmomanometer according to one or more embodiments of the present invention with reference to FIGS. 1 to 10(B). Note that when reference is made to numbers of elements, quantities, and the like with respect to one or more embodiments of the present invention as described below, the scope of the present invention is not necessarily intended to be limited to such numbers of elements, quantities, and the like unless otherwise expressly specified. Also, in the case where multiple embodiments are described below, it is originally expected that the configurations of the embodiments can be appropriately combined unless otherwise expressly specified.

Figure 1:
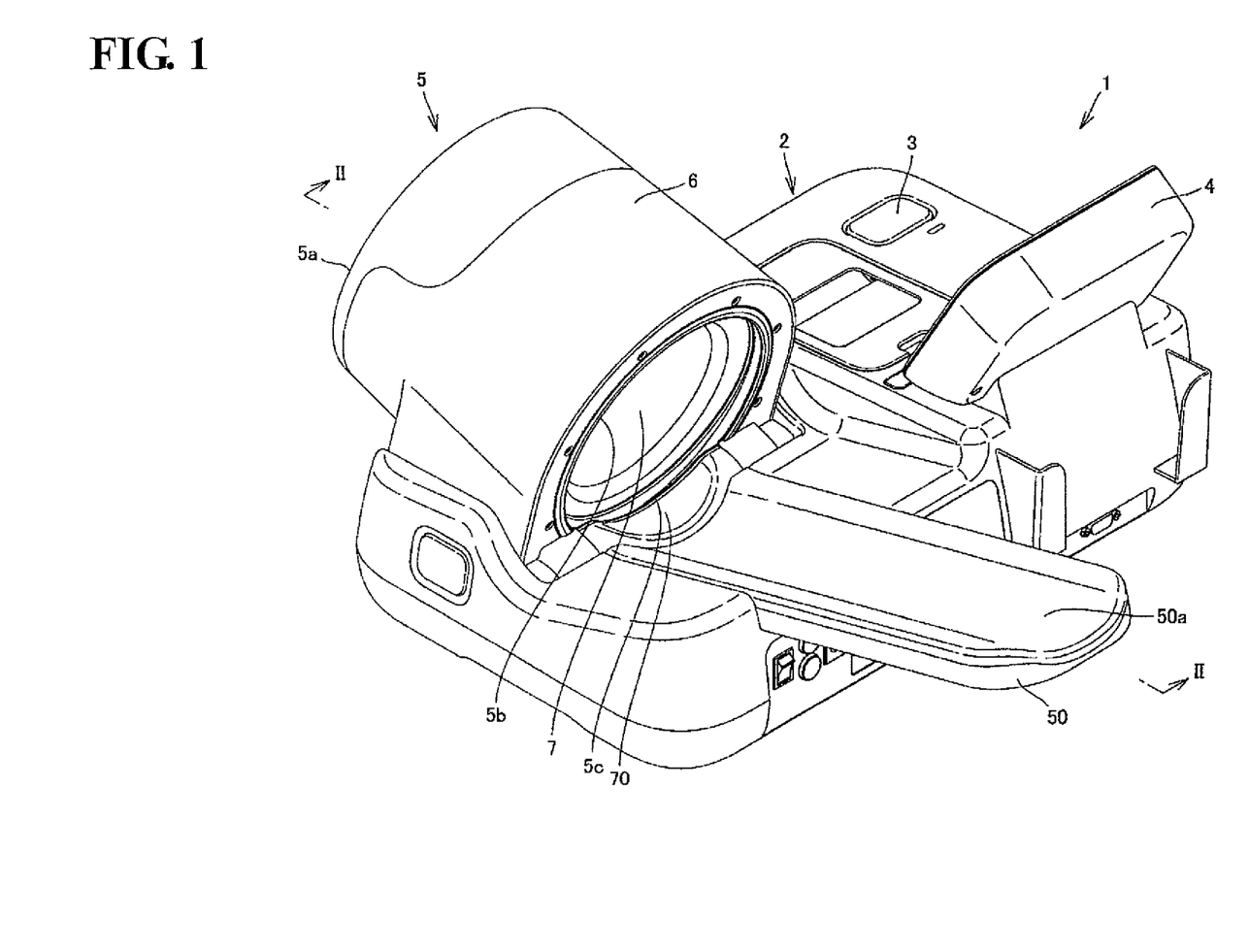
FIG. 1 is a perspective view of the external structure of a sphygmomanometer according to one or more embodiments of the present invention.
Figure 2:
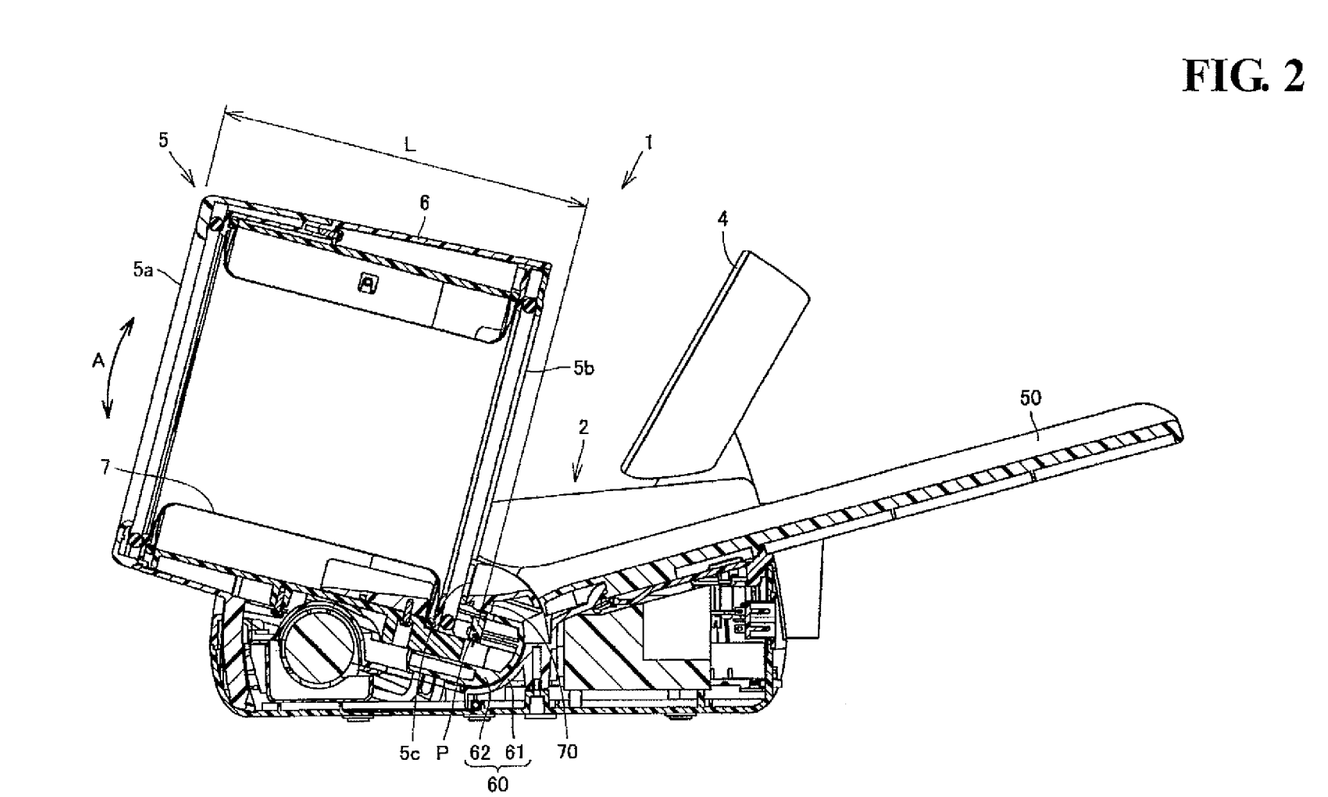
FIG. 2 is a cross-sectional view taken along arrow II-II in FIG. 1 in the case where the inclination angle of a cuff unit is the smallest angle.
Figure 3:
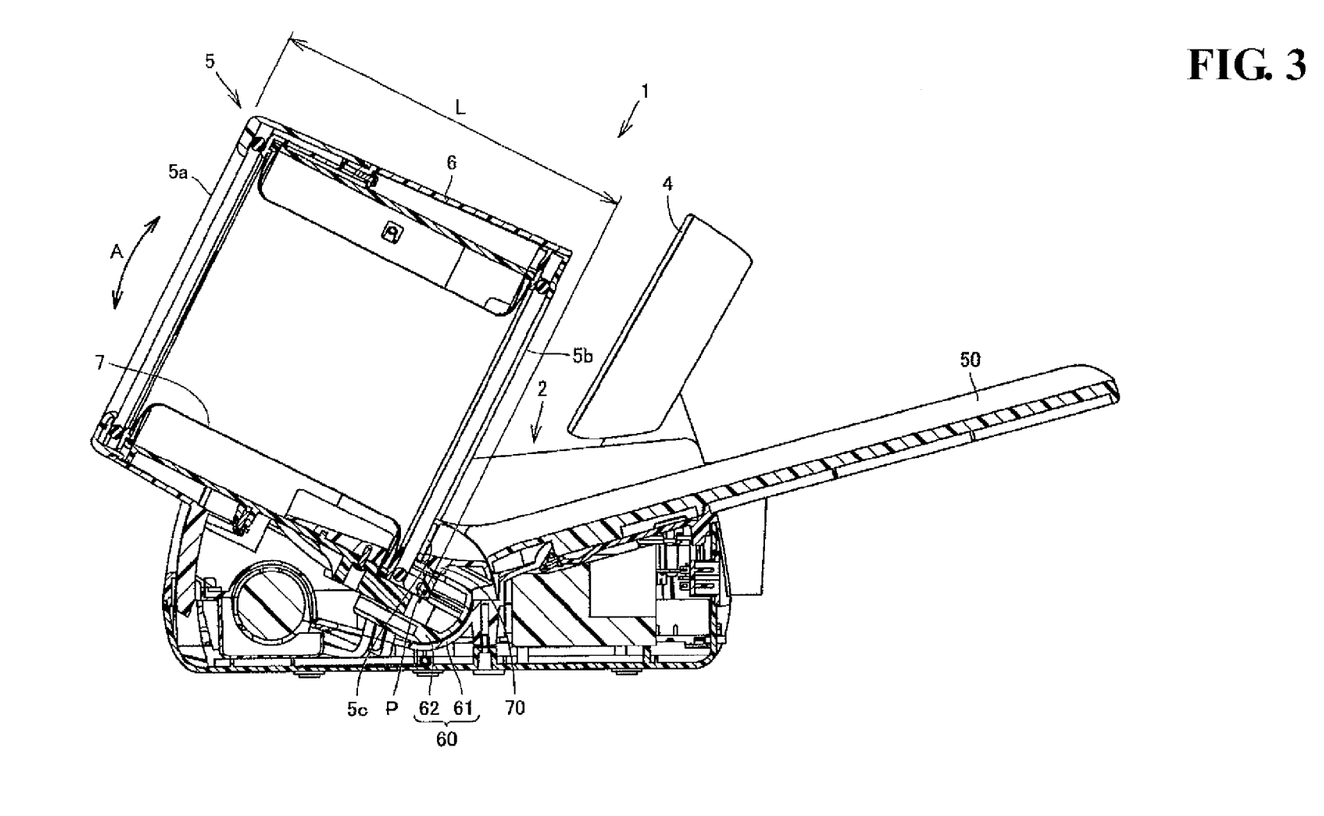
FIG. 3 is a cross-sectional view taken along arrow II-II in FIG. 1 in the case where the inclination angle of the cuff unit is the largest angle.

FIG. 1 is a perspective view of the external structure of a sphygmomanometer according to one or more embodiments of the present invention, FIG. 2 is a cross-sectional view taken along the arrow II-II in FIG. 1 in the case where the inclination angle of a cuff unit is the smallest angle, and FIG. 3 is a cross-sectional view taken along the arrow in FIG. 1 in the case where the inclination angle of the cuff unit is the largest angle.

Configuration of Sphygmomanometer 1

As shown in FIGS. 1 to 3, a sphygmomanometer 1 according to one or more embodiments of the present invention has a base 2 placed on a supporting table such as a desk, and a cuff unit 5 for the insertion of an arm (upper arm) serving as the measurement site. The upper portion of the base 2 is provided with an operation unit 3 on which a power button used for power activation, a measurement button for starting measurement operations, and the like are disposed, and a display unit 4 for displaying measurement results, an operation guide, and the like.

The cuff unit 5 includes a shell 6, which is a substantially cylindrical machine casing, and a biological member compression/fixing mechanism 7 stored in the inner circumferential portion of the shell 6. The cuff unit 5 has an upper arm entrance 5a serving as a biological member entrance, and an upper arm exit 5b serving as a biological member exit. A portion of the base 2 that is positioned below the cuff unit 5 on the upper at arm exit 5b, which is the side opposite to the upper arm entrance 5a, is provided with a rearward-extending arm holder 50 for the placement of an arm. Formed on the surface of the arm holder 50 is a recessed face 50a for limiting horizontal movement of an arm that has been placed thereon and guiding the arm to a placement position.

A rotation mechanism 60 is provided between the cuff unit 5 and the base 2 at a position below the upper arm exit 5b side of the cuff unit 5, and the rotation mechanism 60 enables rotation of the cuff unit 5 relative to the base 2 about a rotation axis P (see FIGS. 2 and 3), within a predetermined inclination angle range. The rotation mechanism 60 includes an arc-shaped base-side guide portion 61 forming a recessed face that is provided centered about the rotation axis P on the base 2 side, and an arc-shaped cuff unit-side guide portion 62 forming a protruding face that is provided centered about the rotation axis P on the cuff unit 5 side.

An elbow detection mechanism 70 that detects the placement of the elbow of the measurement subject is provided in a portion of the cuff unit 5 that is above the rotation axis P. Because this elbow detection mechanism 70 is provided in a portion of the cuff unit 5 that is above the rotation axis P on the upper arm exit 5b side, a distance L between the elbow detection mechanism 70 and the upper arm exit 5b of the cuff unit 5 can be kept constant even when the cuff unit 5 rotates between the case where the inclination angle of the cuff unit 5 is the smallest angle as shown in FIG. 2 and the case where the inclination angle of the cuff unit 5 is the largest angle as shown in FIG. 3. The detailed structure of the elbow detection mechanism 70 will be described later.

Figure 4:
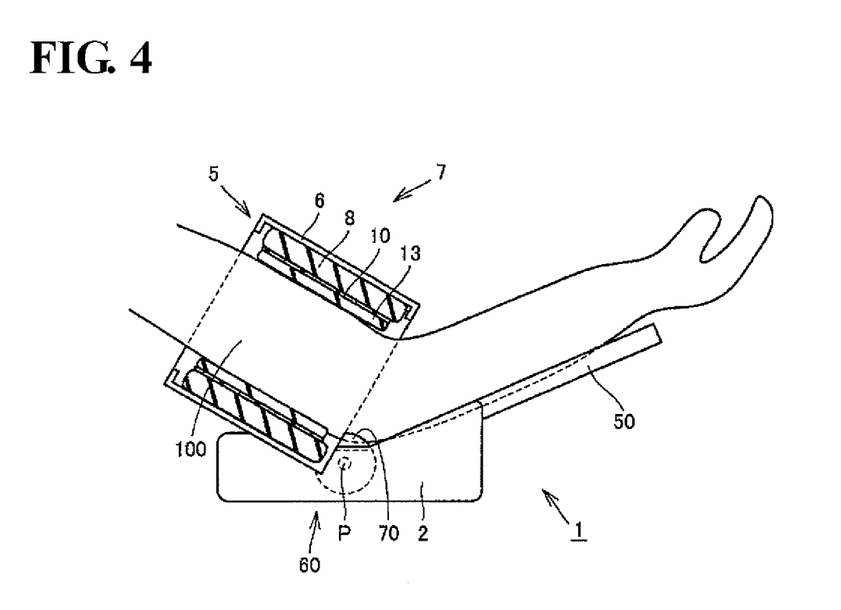
FIG. 4 is a schematic cross-sectional view of a measurement posture in the case of measuring a blood pressure value using the sphygmomanometer shown in FIG. 1.

As shown in FIG. 4, in the case of measuring a blood pressure value using the above-described sphygmomanometer 1, an upper arm 100 of the measurement subject is inserted into the hollow portion located inside the shell 6, the upper arm 100 is compressed and fixed by the biological member compression/fixing mechanism 7 incorporated in the inner circumferential portion of the shell 6, and a blood pressure value is measured.

As shown in FIG. 4, the biological member compression/fixing mechanism 7 of the sphygmomanometer 1 according to one or more embodiments of the present invention includes a biological member compressing air bag 13 serving as a biological member compressing fluid bag for compressing a biological member, a curler 10 that is positioned outside the biological member compressing air bag 13 and serves as a substantially cylindrical flexible member that is extendable in the radial direction, and a curler compressing air bag 8 serving as a flexible member compressing fluid bag that is positioned outside the curler 10 and that, by expanding, presses the outer circumferential face of the curler 10 inward so as to reduce the diameter of the curler 10 and press the biological member compressing air bag 13 against a biological member via the curler 10.

With this sphygmomanometer 1, the upper arm 100 is compressed and fixed by causing the above-described biological member compression/fixing mechanism 7 to operate, and thereafter an arterial pressure pulse wave generated in an artery is detected by causing expansion and contraction of the biological member compressing air bag 13, thereby measuring a blood pressure value.

Functional Blocks of Sphygmomanometer

Figure 5:
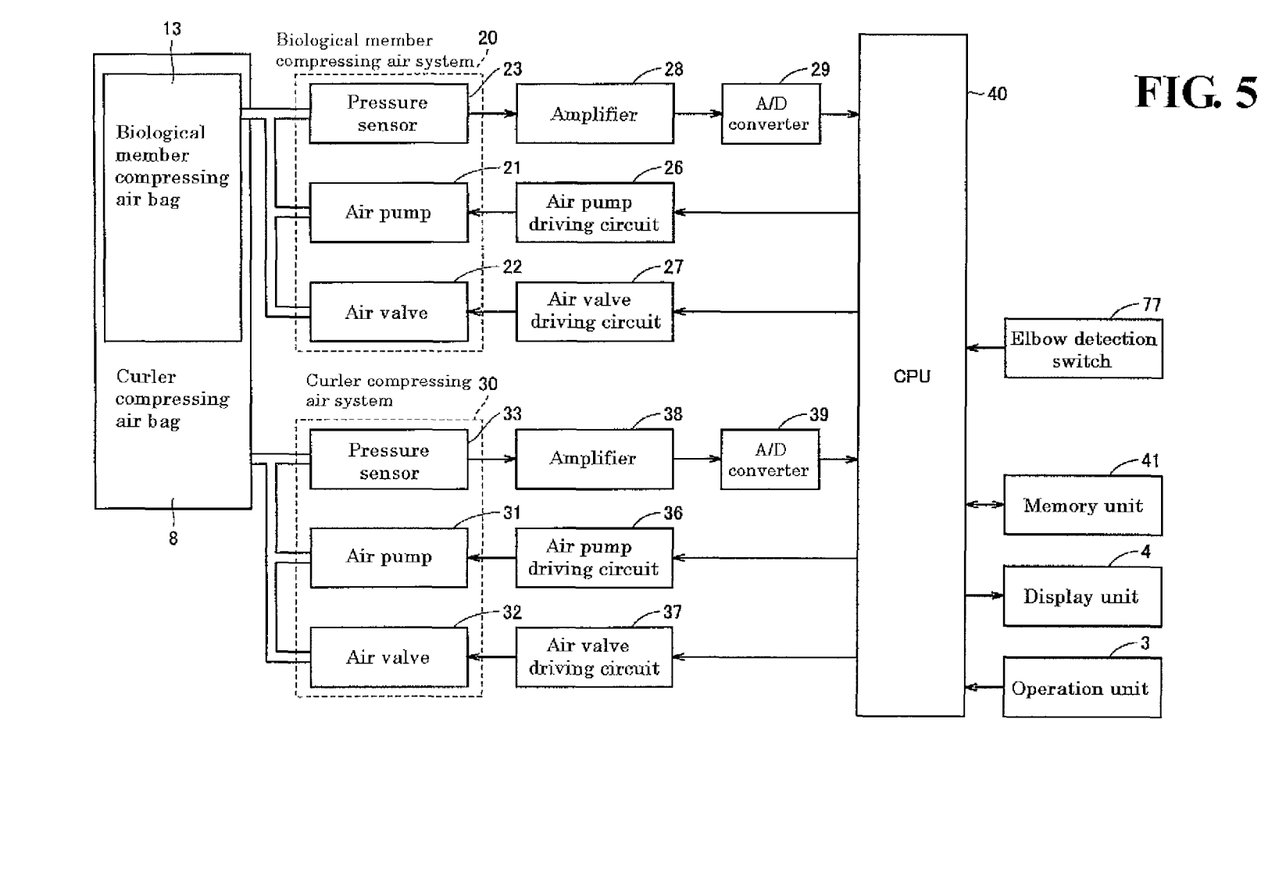
FIG. 5 is a diagram showing functional blocks of the sphygmomanometer shown in FIG. 1.

FIG. 5 is a diagram showing functional blocks of the sphygmomanometer shown in FIG. 1. As shown in FIG. 5, the biological member compressing air bag 13 and the curler compressing air bag 8 described above are, respectively, connected to a biological member compressing air system 20 and a curler compressing air system 30. Also, operations performed by the biological member compressing air system 20 and the curler compressing air system 30 are controlled by a CPU 40.

The biological member compressing air system 20 includes an air pump 21, an air valve 22, and a pressure sensor 23. The air pump 21 is a means for pressurizing the inner cavity of the biological member compressing air bag 13, and an air pump driving circuit 26 that has received a command from the CPU 40 drives the air pump 21 so as to pump a compressed gas into the inner cavity of the biological member compressing air bag 13 such that a predetermined pressure is achieved in the inner cavity during measurement.

The air valve 22 is a means for maintaining or reducing the pressure in the inner cavity of the biological member compressing air bag 13, and an air valve driving circuit 27 that has received a command from the CPU 40 controls the opening and closing of the air valve 22 so as to maintain and reduce the pressure in the inner cavity of the biological member compressing air bag 13 in a high-pressure state achieved by the air pump 21 during measurement, and to return the inner cavity of the biological member compressing air bag 13 to atmospheric pressure after measurement has ended.

The pressure sensor 23 is a means for detecting the pressure in the inner cavity of the biological member compressing air bag 13, and during measurement, the pressure sensor 23 detects the pressure in the inner cavity of the biological member compressing air bag 13, which changes from moment to moment, and outputs a signal in accordance with the detected value to an amplifier 28. The amplifier 28 amplifies the signal output from the pressure sensor 23 and outputs the amplified signal to an A/D converter 29. The A/D converter 29 converts the analog signal output from the amplifier 28 into a digital signal and outputs the digital signal to the CPU 40.

The curler compressing air system 30 includes an air pump 31, an air valve 32, and a pressure sensor 33. The air pump 31 is a means for pressurizing the inner cavity of the curler compressing air bag 8, and an air pump driving circuit 36 that has received a command from the CPU 40 drives the air pump 31 so as to pump a compressed gas into the inner cavity of the curler compressing air bag 8 such that a predetermined pressure is achieved in the inner cavity when measurement starts.

The air valve 32 is a means for maintaining and reducing the pressure in the inner cavity of the curler compressing air bag 8, and an air valve driving circuit 37 that has received a command from the CPU 40 controls the opening and closing of the air valve 32 so as to maintain the pressure in the inner cavity of the curler compressing air bag 8 in a high-pressure state achieved by the air pump 31 during measurement, and to return the inner cavity of the curler compressing air bag 8 to atmospheric pressure after measurement has ended.

The pressure sensor 33 is a means for detecting the pressure in the inner cavity of the curler compressing air bag 8, and when measurement starts, the pressure sensor 33 detects the pressure in the inner cavity of the curler compressing air bag 8 and outputs a signal in accordance with the detected value to an amplifier 38.

The amplifier 38 amplifies the signal output from the pressure sensor 33 and outputs the amplified signal to an A/D converter 39. The A/D converter 39 converts the analog signal output from the amplifier 38 into a digital signal and outputs the digital signal to the CPU 40.

Based on a command input by the operation unit 3 provided on the base 2 of the sphygmomanometer, the CPU 40 controls the biological member compressing air system 20 and the curler compressing air system 30 and outputs measurement results to the display unit 4 and a memory unit 41. Note that the memory unit 41 is a means for storing measurement results. Also, the execution of the control of the sphygmomanometer by the CPU 40 described above is conditional upon the CPU 40 detecting an output signal from a detection switch 77 (described later) with which the elbow detection mechanism 70 is provided.

Measurement Operation Flowchart

Figure 6:
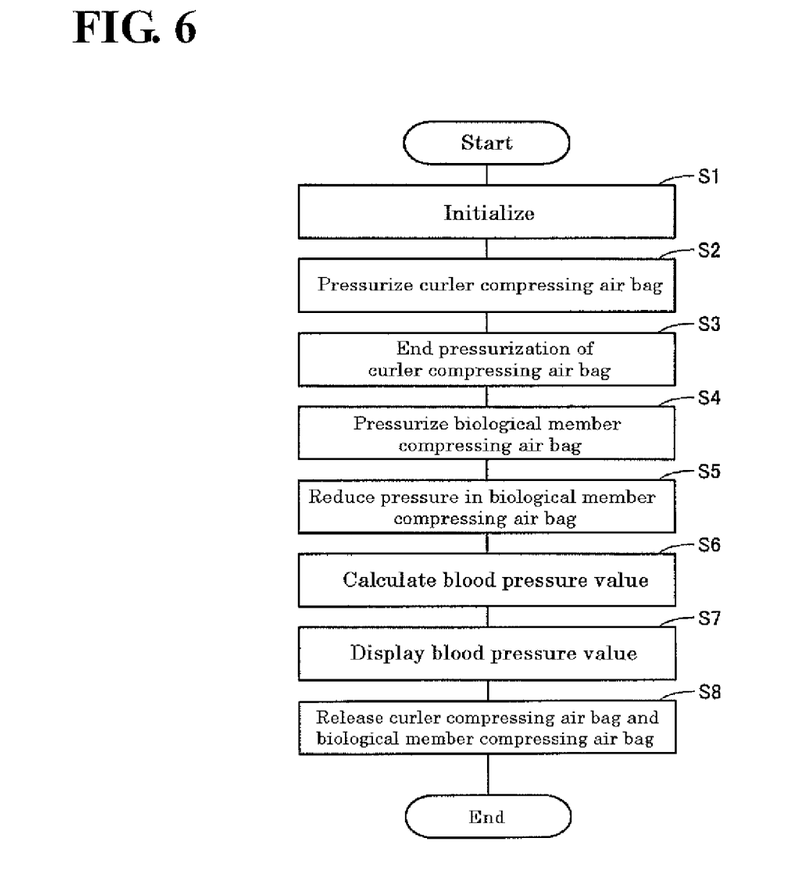
FIG. 6 is a flowchart showing measurement operations performed by the sphygmomanometer shown in FIG. 1.

FIG. 6 is a flowchart showing measurement operations performed by the sphygmomanometer configured as described above. As shown in FIG. 6, measurement operations are started in the sphygmomanometer 1 as a result of the measurement subject or the like pressing a measurement button with which the operation unit 3 of the base 2 is provided. If the elbow detection mechanism 70 has not detected the elbow of the measurement subject, this fact is displayed by the display unit 4, and measurement operations are not started.

First, the sphygmomanometer 1 is initialized in step 1. Next, the curler compressing air bag 8 is pressurized in step 2, and the pressurization of the curler compressing air bag 8 is ended when the pressure in the inner cavity of the curler compressing air bag 8 has reached a predetermined pressure (step 3).

Next, in step 4, the biological member compressing air bag 13 is pressurized, and the pressurization of the biological member compressing air bag 13 is ended when the pressure in the inner cavity of the biological member compressing air bag 13 has reached a predetermined pressure. In step 5, an arterial pressure pulse wave is detected while reducing the pressure in the biological member compressing air bag 13.

Thereafter, in step 6 a blood pressure value is calculated based on the data resulting from the arterial pressure pulse wave detection, in step 7 the blood pressure value is displayed by the display unit 4 with which the base 2 is provided, and in step 8 the inner cavity of the curler compressing air bag 8 and the inner cavity of the biological member compressing air bag 13 are returned to atmospheric pressure.

Elbow Detection Mechanism 70

Next is a description of the structure of the elbow detection mechanism 70 used in the sphygmomanometer 1 according to one or more embodiments of the present invention with reference to FIGS. 7 to 10(B). As described above, the elbow detection mechanism 70 according to one or more embodiments of the present invention is provided in a portion of the cuff unit 5 that is above the rotation axis P, on the upper arm exit 5b side of the cuff unit 5.

Figure 7:
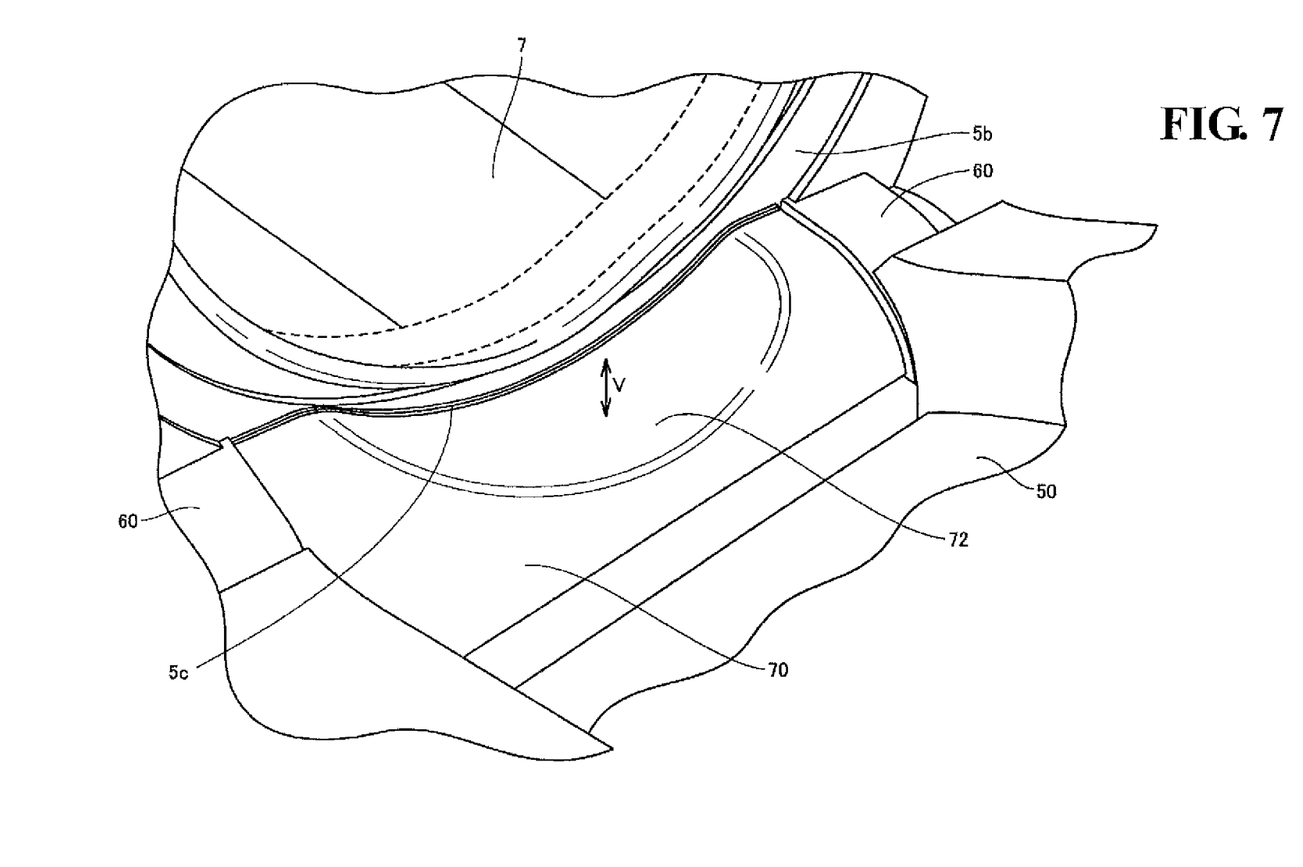
FIG. 7 is an enlarged partial view of an elbow detection mechanism installed in the sphygmomanometer according to one or more embodiments of the present invention.
Figure 8:
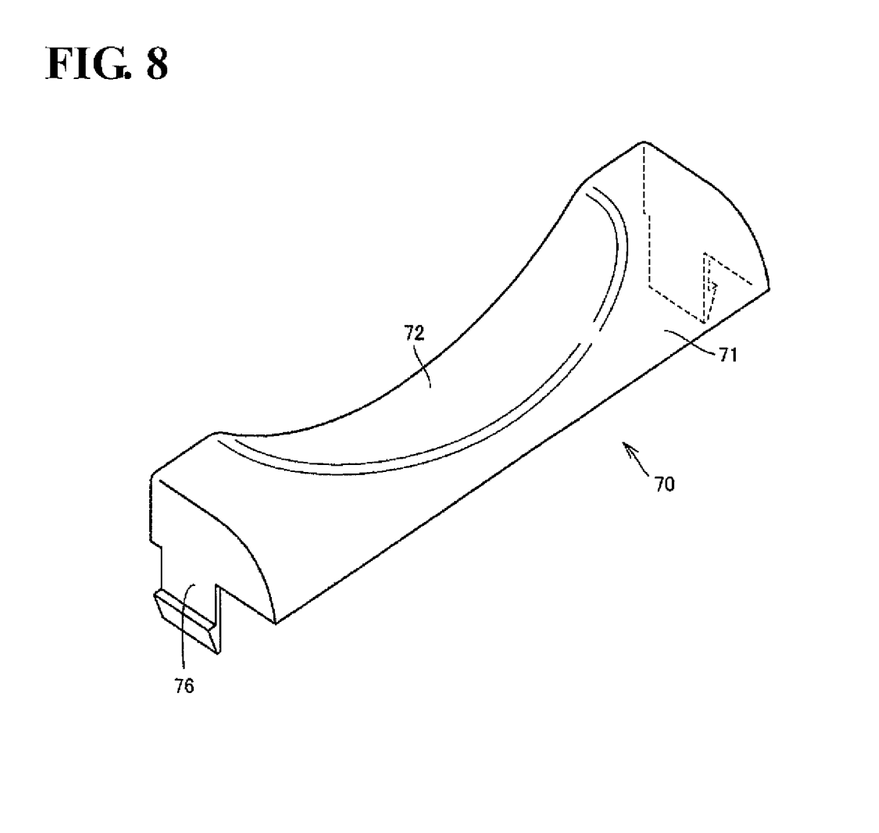
FIG. 8 is an overall perspective view of the top surface side of an elbow detection cover used in the elbow detection mechanism installed in the sphygmomanometer according to one or more embodiments of the present invention.

As shown in FIGS. 7 and 8, the elbow detection mechanism 70 has an elbow detection cover 71 and the detection switch 77 (described later). The elbow detection cover 71 is a rectangular casing whose width is substantially the same as the width of the arm holder 50 on the upper arm exit side 5b. The upper face of the elbow detection cover 71 has a curved shape that is gently inclined from the upper arm exit 5b side toward the arm holder 50, and the upper face is formed so as to have substantially the same curvature as the curvature appearing on the outer surface of the rotation mechanism 60.

A recessed curved face 72 is formed from the center portion of the upper face of the elbow detection cover 71 to both end sides thereof, and the recessed curved face 72 is deepest in the center portion. This recessed curved face 72 is formed so as to be substantially flush with the inner circumferential curved face of the cuff unit 5 on the upper arm exit 5b side. The recessed curved face 72 is also formed so as to be substantially flush with the recessed face 50a with which the arm holder 50 is provided. This eliminates a difference in level between the inner circumferential face of the cuff unit 5 and the upper face of the elbow detection cover 71, thus enabling the measurement subject's arm to be smoothly placed on the elbow detection mechanism 70.

Here, if the surface of the elbow detection cover 71 protrudes beyond the inner circumferential face of the cuff unit 5, there is the possibility of erroneous elbow detection in which a region other than the elbow comes into contact with the elbow detection cover 71 when the upper arm is inserted into the cuff unit 5. In view of this, according to one or more embodiments of the present invention, an erroneous detection prevention wall 5c (see FIGS. 2 and 3) is provided on the upper arm exit 5b side of the cuff unit 5. This erroneous detection prevention wall 5c is provided such that the upper end thereof is at the same height as the outer surface of the elbow detection cover 71. The erroneous detection prevention wall 5c prevents a region other than the elbow from coming into contact with the elbow detection cover 71, thus enabling suppressing erroneous elbow detection.

Figure 9:
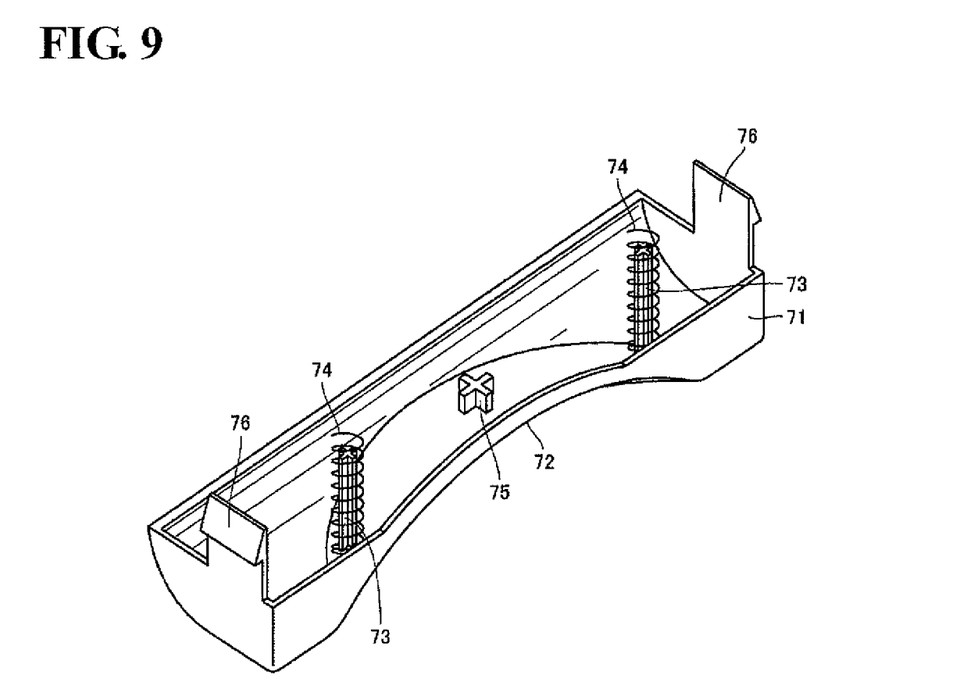
FIG. 9 is an overall perspective view of the bottom surface side of the elbow detection cover used in the elbow detection mechanism installed in the sphygmomanometer according to one or more embodiments of the present invention.

The center portion of the elbow detection cover 71 on the bottom surface side (the most protruding region on the bottom surface side of the recessed curved face 72) is provided with a switch pin 75 that protrudes from the bottom surface side. The turning on and off of the detection switch 77 (described later) is controlled by this switch pin 75. Both side portions of the elbow detection cover 71 on the bottom surface side are each provided with a support pin 73 (together forming a pair) that protrudes from the bottom surface side. A coil spring 74 is fit around each one of the pair of support pins 73. Both side portions of the elbow detection cover 71 are each provided with an engaging claw 76 (together forming a pair) that extends toward the bottom surface side.

When the elbow detection cover 71 is attached on the base 2 side of the main body, the coil springs 74 are guided by the pair of support pins 73 so as to enable vertical movement (the direction of the arrow V in FIG. 7) of the elbow detection cover 71. Also, a configuration in which the elbow detection cover 71 does not become unattached from the base 2 is achieved due to the pair of engaging claws 76 engaging with engagement regions (not shown) with which the base 2 is provided. Normally, the elbow detection cover 71 is lifted upward due to the biasing force of the coil springs 74. When the measurement subject's elbow is placed on the elbow detection cover 71, the elbow detection cover 71 sinks to the base 2 side in resistance to the biasing force of the coil springs 74.

Figure 10A:
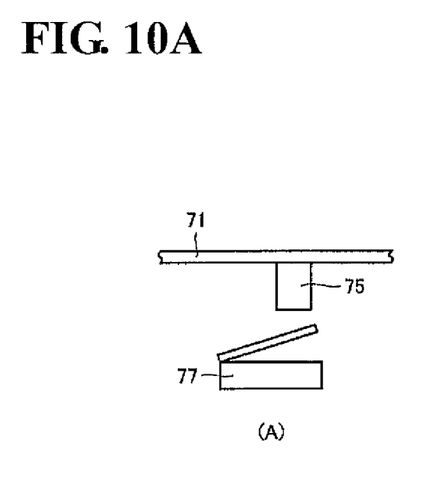
FIG. 10(A) is a first diagram illustrating the positional relationship between a detection switch and the elbow detection cover.
Figure 10B:
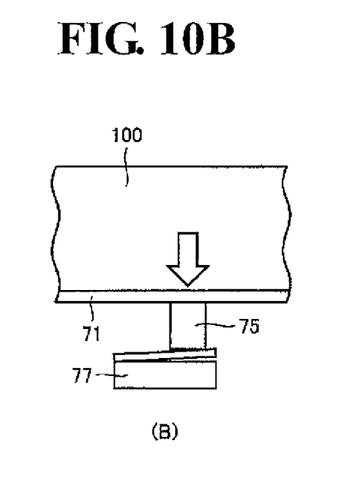
FIG. 10(B) is a second diagram showing the positional relationship between the detection switch and the elbow detection cover.

As shown in FIGS. 10(A) and 10(B), the detection switch 77 is placed in a position below the switch pin 75 on the base 2 side. FIG. 10(A) shows the state in which the elbow detection cover 71 has been lifted upward due to the biasing force of the coil springs 74. The switch pin 75 does not come into contact with the detection switch 77. Accordingly, the detection switch 77 is in the off state.

FIG. 10(B) shows the state in which the measurement subject's upper arm 100 has been placed on the elbow detection cover 71, and the elbow detection cover 71 has been pressed down to the base 2 side (rotation axis P side) in resistance to the biasing force of the coil springs 74. The switch pin 75 has come into contact with the detection switch 77. Accordingly, the detection switch 77 is in the on state.

In this way, because the elbow detection mechanism 70 is provided in a portion above the rotation axis P in the sphygmomanometer 1 according to one or more embodiments of the present invention, the distance L between the elbow detection mechanism 70 and the upper arm exit 5b of the cuff unit 5 can be kept constant even when the cuff unit 5 rotates between the case where the inclination angle of the cuff unit 5 is the smallest angle as shown in FIG. 2 and the case where the inclination angle of the cuff unit 5 is the largest angle as shown in FIG. 3.

As a result, the distance (L) between the elbow detection mechanism 70 and the upper arm entrance 5a of the cuff unit 5 can be kept constant regardless of the inclination angle of the cuff unit 5 relative to the base 2. This enables guiding the measurement subject to the appropriate measurement posture regardless of the measurement subject's physique. This also makes it possible to provide accurate blood pressure value measurement results for a wide range of measurement subjects, thus enabling widespread use in hospitals, public facilities, and the like.

Note that although the example where the elbow detection mechanism according to one or more embodiments of the present invention is installed in a sphygmomanometer in which the curler compressing air bag is disposed on the outer circumferential face of the curler, and the biological member compressing air bag is disposed on the inner circumferential face of the curler is described in the above embodiment, the elbow detection mechanism according to one or more embodiments of the present invention can be installed in any sphygmomanometer including a rotation mechanism for enabling rotation of the cuff unit relative to the base.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

REFERENCE NUMERALS 1 sphygmomanometer
2 base
3 operation unit
4 display unit
5 cuff unit
5a upper arm entrance
5b upper arm exit
5c erroneous detection prevention wall
6 shell
7 biological member compression/fixing mechanism
8 curler compressing air bag
10 curler
13 biological member compressing air bag
20 biological member compressing air system
21, 31 air pump
22, 32 air valve
23, 33 pressure sensor
26, 36 air pump driving circuit
27, 37 air valve driving circuit
28, 38 amplifier
29, 39 A/D converter
30 curler compressing air system
40 CPU
41 memory unit
50 arm holder
50a recessed face
60 rotation mechanism
61 base-side guide portion
62 cuff unit-side guide portion
70 elbow detection mechanism
71 elbow detection cover
72 recessed curved face
73 support pin
74 coil spring
75 switch pin
76 engaging claw
77 detection switch
100 upper arm
P rotation axis

The invention claimed is:
1. A sphygmomanometer comprising:
a base;
a cuff unit into which a biological member serving as a measurement site can be inserted;
a rotation mechanism that is provided between the base and a position below a biological member exit side of the cuff unit and enables rotation of the cuff unit relative to the base about a rotation axis;
an elbow detection mechanism that is provided in a portion of the cuff unit above the rotation axis and detects placement of an elbow of a measurement subject,
wherein the elbow detection mechanism includes an elbow detection cover adapted to receive the elbow of the measurement subject, wherein an upper surface of the elbow detection cover comprises a recessed curved face that is substantially flush with an inner surface of the cuff unit on the biological member exit side of the cuff unit; and
an erroneous detection prevention wall, whose upper end is at a same height as that of an outer surface of the elbow detection cover, that is provided on the biological member exit side of the cuff unit.

* * * * *